(12) United States Patent
Mayo et al.

(10) Patent No.: US 11,434,219 B2
(45) Date of Patent: Sep. 6, 2022

(54) PURIFICATION OF CANNABINOIDS FROM CRUDE CANNABIS OIL

(71) Applicant: TABA IP, LLC, Detroit, MI (US)

(72) Inventors: Joshua Mayo, Detroit, MI (US); Aaron Rieder, Detroit, MI (US)

(73) Assignee: TABA IP, LLC, Detroit, MI (US)

( * ) Notice: Subject to any disclaimer, the term of this patent is extended or adjusted under 35 U.S.C. 154(b) by 47 days.

(21) Appl. No.: 16/915,631

(22) Filed: Jun. 29, 2020

(65) Prior Publication Data

US 2021/0078968 A1 Mar. 18, 2021

Related U.S. Application Data

(62) Division of application No. 16/298,646, filed on Mar. 11, 2019, now Pat. No. 10,696,646.

(60) Provisional application No. 62/747,651, filed on Oct. 18, 2018.

(51) Int. Cl.
*C07D 311/80* (2006.01)
*C11B 1/10* (2006.01)
*C11B 3/00* (2006.01)

(52) U.S. Cl.
CPC .............. *C07D 311/80* (2013.01); *C11B 1/10* (2013.01); *C11B 3/008* (2013.01); *C07B 2200/13* (2013.01)

(58) Field of Classification Search
CPC .................... C07D 311/80; C07B 2200/13
See application file for complete search history.

(56) References Cited

U.S. PATENT DOCUMENTS

| | | | |
|---|---|---|---|
| 9,044,390 | B1 | 6/2015 | Speier |
| 10,696,646 | B2 * | 6/2020 | Mayo ..................... C11B 3/008 |
| 2002/0086438 | A1 | 7/2002 | Elsohly et al. |
| 2005/0266108 | A1 | 12/2005 | Flockhart et al. |
| 2016/0228385 | A1 | 8/2016 | Sievers et al. |
| 2016/0326130 | A1 | 11/2016 | Changoer et al. |
| 2017/0008870 | A1 | 1/2017 | Dibble et al. |
| 2017/0349518 | A1 | 12/2017 | Dickman et al. |
| 2018/0162828 | A1 | 6/2018 | Nadal Roura |
| 2018/0273501 | A1 | 9/2018 | Robertson et al. |
| 2018/0333446 | A1 | 11/2018 | Shan et al. |
| 2018/0344785 | A1 * | 12/2018 | Robertson .............. A61K 36/18 |
| 2019/0010106 | A1 | 1/2019 | Oroskar et al. |
| 2019/0160393 | A1 | 5/2019 | Marshall et al. |
| 2020/0001201 | A1 * | 1/2020 | Noble .................. B01D 9/0054 |

FOREIGN PATENT DOCUMENTS

| | | |
|---|---|---|
| GB | 2408978 | 6/2005 |
| WO | 2004/026857 | 4/2004 |
| WO | 2016/116628 | 7/2016 |
| WO | 2016153347 | 9/2016 |

OTHER PUBLICATIONS

Skell; Acta Crystallographica, Section C: Structural Chemistry 2021, 77, 84-89. DOI: 10.1107/s2053229621000280 (Year: 2021).*

(Continued)

*Primary Examiner* — Daniel R Carcanague
(74) *Attorney, Agent, or Firm* — McDonnell Boehnen Hulbert & Berghoff LLP (57) ABSTRACT

The present disclosure is generally directed to methods for purifying cannabinoids from *Cannabis* plants.

5 Claims, 2 Drawing Sheets

(56) References Cited

OTHER PUBLICATIONS

Rosenqvist; Acta Chem Scand B. 1975, 29, 379-384. DOI: 10.3891/acta.chem.scand.29b-0379 (Year: 1975).*
Anonymous: "Acetone crystallization of THC-A-Hash and Stuff/THCa Crystallization—Future4200", Mar. 1, 2018 (Mar. 1, 2018), XP055599185, Retrieved from the internet: URL:https://future4200.com/t/acetone-crystallization-of-thc-a/136 [retrieved on Jun. 25, 2019].
International Search Report and Written Opinion for International Appl. No. PCT/US2019/021621, dated Jul. 10, 2019.
Appendino; Current Medicinal Chemistry, 2011, 18, 1085-1099. (Year: 2011).
Korte; Angewandte Chemie 1965, 77, 862. (Year: 1965).
Lehmann; Phytochemical Analysis 1992, 3, 88-90. (Year: 1992).
Mechoulam; Chem. Rev. 1976, 76, 75-112. (Year: 1976).
Rovetto; J .of Supercritical Fluids 2017, 129, 16-27. (Year: 2017).
Smith; J. Pharm. Pharmac., 1971,29,286-290. (Year: 1971).
Wohlfarth; J .Chromatogr. B 2011 879, 3059-3064. Doi: 10.1016/j.jchromb.2011.09.012 (Year: 2011).

* cited by examiner

PURIFICATION OF CANNABINOIDS FROM CRUDE CANNABIS OIL

CROSS-REFERENCE TO RELATED APPLICATIONS

This application is a divisional application of U.S. patent application Ser. No. 16/298,646, filed Mar. 11, 2019, which claims the benefit of priority of U.S. Provisional Application No. 62/747,651, filed Oct. 18, 2018, all of which are hereby incorporated by references in their entirety.

BACKGROUND OF THE DISCLOSURE

Field of the Invention

The present disclosure is generally directed to methods for purifying cannabinoids from *Cannabis* plants.

Description of the Related Art

Every individual has an endocannabinoid system comprised of chemical receptors in the brain, immune system, and central nervous system, for example, cannabinoid 1 (CB1) receptor and cannabinoid 2 (CB2) receptor. CB1 and CB2 receptors are members of the G protein-coupled receptor (GPCR) superfamily. The CB1 receptor is expressed in the central nervous system (CNS), lungs, liver, adipose tissue, and kidneys, and the CB2 receptor is mainly localized in immune cells and on cells that are involved in bone formation and bone loss. These receptors have been associated with many human diseases including obesity, diabetes, fibrosis, liver diseases, cardiovascular disease, cancer, pain, MS spasticity, and glaucoma, among others.

Cannabinoids are compounds active on cannabinoid receptors in humans and have been implicated in many of the pharmacological benefits on the diseases noted above. Cannabinoids of plant origin, also known as phytocannabinoids, are abundant in *Cannabis*. Medical use of *cannabis* and associated phytocannabinoids is becoming widely accepted in the United States as an alternative form of medicine. Many states have legalized its use for qualified medical conditions such as chronic pain, epilepsy, sleep disorders, anxiety, cancer, glaucoma, nausea, amyotrophic lateral sclerosis (ALS), Alzheimer's disease, Crohn's disease, Post-traumatic Stress Disorder (PTSD), arthritis, fibromyalgia, and others.

One of the most common ways that *cannabis* is used for medicinal use in many countries is through smoking. Although proven to be beneficial in certain indications, smoking medical *cannabis* has disadvantages. For example, the smoke from the plant matter comprises carcinogens and other toxins in addition to the desired cannabinoids. Heavy *cannabis* use through smoking has also been associated with accelerated pulmonary decline, lung damage, and emphysema. Another disadvantage of smoking medical *cannabis* is difficulty in maintaining control over the proper dosing of medicinal *cannabis* due to active ingredients fluctuations (e.g., the amounts of active ingredients may differ depending on the differences present in plant varietals as well as changing growing conditions which result in intravarietal variations.) Finally, consumption through smoking has a relatively low bioavailability of target compounds compared to other delivery methods.

A less common way to utilize *cannabis* for medical use is to extract beneficial cannabinoids from *cannabis*. Many extraction processes have been developed for isolating and purifying cannabinoids. But there has been difficulty in isolating individual cannabinoids at high levels of purity, both for active ingredients for use in medicine and product manufacturing and/or as standards for use in research and development. This is because extraction and purification methods usually provide a low yield of the desired isoprenoid, as biological materials typically contain only small quantities of these compounds.

Therefore, there exists a need for simple, economical, and reliable methods that provide a high purity of cannabinoids.

SUMMARY OF THE DISCLOSURE

The disclosure provides methods for purifying cannabinoids from a mixture (such as from *Cannabis* plant material). Such methods generally include: providing the mixture and one or more solvents to obtain a solution of the extract; maintaining the solution at a temperature of up to 25° C. for a time sufficient to obtain solid cannabinoid; and removing the one or more solvents to obtain pure cannabinoid.

In certain embodiments of this aspect, the method of the disclosure is a method of purifying a cannabinoid from a *Cannabis* plant material, the method including:

providing the *Cannabis* plant material and one or more solvents selected from of N,N-dimethylacetamide (DMA), N,N-dimethylformamide (DMF), tetrahydrofuran (THF), and combination thereof to obtain a solution of the extract;

maintaining the solution at a temperature between −40° C. to 25° C. for a time sufficient to obtain solid cannabinoid; and removing the one or more solvents to obtain pure cannabinoid.

Another aspect of the disclosure provides a cannabinoid prepared according to method of the disclosure as described herein.

In certain embodiments of this aspect, the cannabinoid is tetrahydrocannabinolic acid (THCA, THCa, $\Delta^9$-tetrahydrocannabinolic acid, or $\Delta^9$-THCA), cannabidiolic acid (CBDA or CBDa), cannabidiol (CBD), tetrahydrocannabivarin (THCV or THV), or a combination thereof. In certain embodiments of this aspect, the cannabinoid is tetrahydrocannabinolic acid. In certain embodiments of this aspect, the cannabinoid is crystalline tetrahydrocannabinolic acid Form A as described herein.

In certain embodiments of this aspect, the cannabinoid prepared according to method of the disclosure as described herein has a purity of at least 95%.

Another aspect of the disclosure provides methods of preparing a pure cannabinol. Such methods include heating the pure cannabinoid prepared according to method of the disclosure as described herein to a temperature sufficient to decarboxylate the cannabinoid.

In certain embodiments of this aspect, such methods include providing the *Cannabis* plant material and one or more solvents selected from of N,N-dimethylacetamide, N,N-dimethylformamide, tetrahydrofuran, and combination thereof to obtain a solution of the extract;

maintaining the solution at a temperature between −40° C. to 25° C. for a time sufficient to obtain solid cannabinoid;

removing the one or more solvents to obtain a pure cannabinoid; and heating the pure cannabinoid to a temperature sufficient to decarboxylate the cannabinoid to obtain the pure cannabinol.

In certain embodiments of this aspect, the cannabinol prepared according to method of the disclosure as described herein has a purity of at least 95%. In certain embodiments of this aspect, the cannabinol prepared according to method of the disclosure as described herein has a purity of at least 98%.

Another aspect of the disclosure provides a cannabinol having a purity of at least 96%, wherein the cannabinoid is prepared according to method of the disclosure as described herein.

In certain embodiments of this aspect, the cannabinol is tetrahydrocannabinol (THC, $\Delta^9$-tetrahydrocannabinol, or $\Delta^9$-THC) or cannabidiol (CBD). In certain other embodiments of this aspect, the cannabinol is tetrahydrocannabinol. In certain embodiments of this aspect, the cannabinoid is crystalline tetrahydrocannabinolic acid Form A as described herein.

Another aspect of the disclosure provides crystalline tetrahydrocannabinolic acid Form A as described herein.

BRIEF DESCRIPTION OF THE DRAWINGS

The accompanying drawings are included to provide a further understanding of the compositions and methods of the disclosure, and are incorporated in and constitute a part of this specification. The drawings are not necessarily to scale, and sizes of various elements may be distorted for clarity. The drawings illustrate one or more embodiment(s) of the disclosure, and together with the description serve to explain the principles and operation of the disclosure.

DETAILED DESCRIPTION

The particulars shown herein are by way of example and for purposes of illustrative discussion of certain embodiments of the present invention only and are presented in the cause of providing what is believed to be the most useful and readily understood description of the principles and conceptual aspects of various embodiments of the disclosure. In this regard, no attempt is made to show structural details of the invention in more detail than is necessary for the fundamental understanding of the invention, the description taken with the examples making apparent to those skilled in the art how the several forms of the disclosure may be embodied in practice. Thus, before the disclosed compositions and methods are described, it is to be understood that the aspects described herein are not limited to specific embodiments, or configurations, and as such can, of course, vary. It is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. In addition, the terminology used herein is for the purpose of describing particular aspects only and, unless specifically defined herein, is not intended to be limiting. Accordingly, the present disclosure is not limited to that precisely as shown and described.

As used herein, the singular forms "a", "an" and "the" include plural referents unless the context clearly dictates otherwise. "And" as used herein is interchangeably used with "or" unless expressly stated otherwise.

As used herein, "about" means±five percent (5%) of the recited unit of measure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification.

In view of the present disclosure, the methods and compositions described herein can be configured by the person of ordinary skill in the art to meet the desired need. In general, the disclosed methods and compositions provide improvements in purification of cannabinoids from *Cannabis* plant materials. Specifically, the inventors found that cooling crystallization allows for controlled cannabinoid crystal growth from various cannabinoid sources, regardless of the quality of the source or concentration of the cannabinoid in the source. The method of the disclosure, in certain embodiments, is efficient and economical as it limits the amount of the solvent used in the method. For example, the method of the disclosure allows for higher ratio of the solute to the solvent (i.e., less solvent is used), no solvent is removed during crystallization, and the removed solvent in order to obtain the pure material can be recycled. Moreover, in certain embodiments, the method of the disclosure provides highly pure cannabinoids, e.g. at least 95% pure, having improved appearance, e.g., no residual yellow color upon visual inspection.

In contrast, the current commercial and known purification methods utilizing single-solvent or multi-solvent evaporative crystallization with, e.g., hexane, pentane, heptane, etc., achieve crystallization yields of 35% to 50%. Some evaporative crystallization methods using ethanol and hydrocarbons can have THCa potencies of up to 85%. But these solvents are nonselective and result in a product that is generally a mixture of many different cannabinoids as well as lipids, terpenes and other similar molecules. Furthermore, evaporative crystallization provides very limited control over nucleation and crystal growth, often resulting in decreased purity while requiring larger amounts of solvent, much of which is not being recovered.

Cannabinoids of the present disclosure include any one of substances that are structurally related to tetrahydrocannabinol and that bind to a cannabinoid receptor such as CB1, CB2, or both. The cannabinoid can be a naturally occurring compound (e.g. present in *Cannabis*), a compound metabolized by a plant or animal, or a synthetic derivative. Cannabinoid of the present disclosure include salts or solvates of the active substances.

Accordingly, one aspect of the disclosure provides a method of purifying a cannabinoid from a mixture, the method including:
providing the mixture and one or more solvents to obtain a solution of the extract;
maintaining the solution at a temperature of up to 25° C. for a time sufficient to obtain solid cannabinoid; and removing the one or more solvents to obtain pure cannabinoid.

In certain embodiments, the cannabinoid of the disclosure is naturally occurring compound. For example, the cannabinoid of the disclosure is present in *Cannabis* plant material. As used herein, *Cannabis* includes any species having desired cannabinoid content, such as *Cannabis indica*, *Cannabis sativa*, and *Cannabis ruderalis*. In certain embodiments of the methods as described herein, the *Cannabis* plant material is *Cannabis indica* plant material. In certain embodiments of the methods as described herein, the *Cannabis* plant material is *Cannabis sativa* plant material. In certain embodiments of the methods as described herein, the *Cannabis* plant material is *Cannabis ruderalis* plant material.

One of skill in the art recognizes that any part of the plant having desired cannabinoid content may be used in the methods of the disclosure. In certain embodiments, the plant material is plant extract, such as plant oil.

As noted above, the methods include maintaining the solution of the extract at a temperature of up to 25° C. One of skill recognizes that the lower limit for the temperature at which the solution is maintained is above the freezing point for the one or more solvents. For example, if the freezing point of the one or more solvents is −60° C., then the solution is maintained at a temperature above −60° C. and up to 25° C.

One specific embodiment of the methods of the disclosure provides a method of purifying a cannabinoid from a *Cannabis* plant material. Such method includes:
providing the *Cannabis* plant material and one or more solvents selected from of N,N-dimethylacetamide, N,N-dimethylformamide, tetrahydrofuran, and combination thereof to obtain a solution of the extract;
maintaining the solution at a temperature between −40° C. to 25° C. for a time sufficient to obtain solid cannabinoid; and
removing the one or more solvents to obtain pure cannabinoid.

In certain embodiments, the methods of the disclosure as described herein are particularly suitable for obtaining tetrahydrocannabinolic acid, cannabidiolic acid, cannabidiol, tetrahydrocannabivarin, or a combination thereof. In certain embodiments, the methods of the disclosure as described herein are particularly suitable for obtaining tetrahydrocannabinolic acid.

The methods of the disclosure as described herein, in certain embodiments, obtain a cannabinoid in crystalline form. For example, in certain embodiments, the methods of the disclosure result in tetrahydrocannabinolic acid are in crystalline form.

In certain embodiments, the cannabinoid of the disclosure is crystalline tetrahydrocannabinolic acid (as N,N-dimethylacetamide solvate) herein identified as Form A. The crystalline tetrahydrocannabinolic acid Form A of the disclosure is characterized in that it provides the following cell unit parameters: space group is $P2_12_12_1$, cell dimensions are: a=9.4279(2) Å, b=10.8422(2) Å, c=25.2168(4) Å, α=β=γ=90°, and number of formula units are 4. The single crystal X-Ray diffraction data as disclosed herein was obtained by standard techniques using XtaLAB Synergy-S/Rigaku Oxford diffractometer operating with a Cu Kα radiation source at 50 kV, 1 mA, and temperature of measurement 298.60(10) K during data collection.

In certain embodiments, the crystalline tetrahydrocannabinolic acid Form A of the disclosure is characterized in that it provides a XRPD pattern comprising a peak at about 6.9 (2θ degrees). In certain embodiments of Form A of the disclosure, the XRPD pattern further includes peaks at about 11.6 and about 14.0 (2θ degrees). In certain embodiments of Form A of the disclosure, the XRPD pattern further includes peaks at about 20.8 and about 21.6 (2θ degrees). In certain embodiments of Form A of the disclosure, the XRPD pattern further includes peaks at about 14.2, about 16.6, about 18.7, about 19.9, about 23.5, and about 24.9 (2θ degrees). XRPD data as disclosed herein was obtained by standard techniques using using Rigaku MiniFlex 600 diffractometer operating with a Cu Kα radiation source at 40 kV, 15 mA, step size 0.02° 2θ.

In certain embodiments, the cannabinoid of the disclosure is crystalline tetrahydrocannabinolic acid (as N,N-dimethylacetamide solvate) Form A characterized in that it provides a XRPD pattern comprising peaks at about 6.9, about 11.6, and about 14.0 (2θ degrees). In certain embodiments, Form A of the disclosure is characterized in that it provides a XRPD pattern comprising peaks at about 6.9, about 11.6, about 14.0, about 20.8 and about 21.6 (2θ degrees). In certain embodiments, Form A of the disclosure is characterized in that it provides a XRPD pattern comprising at 6.9, about 11.6, about 14.0, about 14.2, about 16.6, about 18.7, about 19.9, about 20.8, about 21.6, about 23.5, and about 24.9 (2θ degrees).

The present inventors have determined that the methods of the disclosure as described herein provide pure cannabinoid. Thus, in certain embodiments, the cannabinoid (such as tetrahydrocannabinolic acid) has purity of at least 95%. For example, in certain embodiments, the purity is at least 96%; or at least 97%; or at least 98%; or at least 99%; or at least 99.5%; or at least 99.9%. The inventors have also determined that the methods of the disclosure as described herein provide pure cannabinoid in high yield based on the content of the cannabinoid in the plant material. Thus, in certain embodiments, the cannabinoid (such as tetrahydrocannabinolic acid) is obtained in yield of at least 75%; or at least 76%; or at least 80%; or at least 85%; or at least 90%; or at least 99.9%.

As noted above, in certain embodiments of the methods of the disclosure as disclosed herein, the one or more solvents is selected from of N,N-dimethylacetamide, N,N-dimethylformamide, tetrahydrofuran, and combination thereof. In some embodiments, the one or more solvents is selected from of N,N-dimethylacetamide, N,N-dimethylformamide, and combination thereof. In some embodiment, the one or more solvents is selected from of N,N-dimethylacetamide, tetrahydrofuran, and combination thereof. In some embodiments, the one or more solvents is selected from of N,N-dimethylformamide, tetrahydrofuran, and combination thereof.

In certain embodiments of the methods of the disclosure as disclosed herein, the one or more solvents is selected from of N,N-dimethylacetamide, N,N-dimethylformamide, tetrahydrofuran, and combination thereof, and further comprises water. For example, in certain embodiments, the one or more solvents comprises N,N-dimethylacetamide and water.

Some embodiments of the methods of the disclosure as disclosed herein are those wherein the one or more solvents is N,N-dimethylacetamide.

In some embodiments of the methods of the disclosure as disclosed herein, the one or more solvents is N,N-dimethylformamide.

Some embodiments of the methods of the disclosure as disclosed herein are those wherein the one or more solvents is tetrahydrofuran.

As noted above, the present inventors have determined that the method of the disclosure requires lower amount of solvent (i.e., higher concentration of the plant material in the solvent) compared to the evaporative crystallization methods. For example, in certain embodiments, the *Cannabis* plant material (e.g., extract) and the one or more solvents are provided in a weight ratio in a range of 5:1 and 1:5. In certain other embodiments, the plant material and the one or more solvents are provided in a weight ratio in a range of 1:1 and 1:5; or in a range of 4:1 and 1:4; or in a range of 1:1 and 1:4; or in a range of 3:1 and 1:3; or in a range of 1:1 and 1:3; or in a range of 2:1 and 1:2; or in a range of 1:1 and 1:2; or in a range of 1.5:1 and 1:1.5; or in a range of 1:1 and 1:1.5; or in a range of 1.3:1 and 1:1.3; in a range of 1:1 and 1:1.3; or in a range of 1.1:1 and 1:1.1. In certain other embodiments, the plant material and the one or more solvents are provided in a weight ratio of about 1:1.

Because the methods of the disclosure generally require less solvent, in certain embodiments, the methods comprise providing the plant material and the one or more solvents are under mixing at a temperature between 25° C. to 80° C., or between 30° C. to 50° C., for a time sufficient to prepare the solution. Such time may be up to 1 minute, up to 5 minutes, up to 10 minutes, up to 15 minutes, up to 20 minutes, up to 30 minutes, up to 1 hour, and even up to 2 hours. In certain embodiments, the pressure is less than 1 atm, e.g., 0.75 atm, or 0.5 atm.

The methods of the disclosure as disclosed herein may further comprise providing a cannabinoid seed crystal to the solution of the extract, prior to maintaining it.

The solution of the extract is maintained at temperature of up to 25° C. In particular embodiments, the temperature is sufficiently low in order to allow cooling crystallization of the cannabinoid. In certain embodiments of the methods of the disclosure as disclosed herein, the solution is maintained at a temperature between −40° C. to −20° C.; or −40° C. to −25° C.; or −35° C. to −20° C.; or −35° C. to −25° C.; or −33° C. to −27° C.; or −32° C. to −28° C. Some embodiments of the methods of the disclosure as disclosed herein are those wherein the solution is maintained at a temperature of about −30° C.

The solution of the extract is maintained for a period of time sufficient to form solid cannabinoid. In certain embodiments, the solution of the extract is maintained for a period of up to 6 hours, up to 8 hours, up to 12 hours, or 1 to 6 hours, or 1 to 8 hours, or 1 to 12 hours, 12 to 72 hours; or 24 to 48 hours; or 30 to 42 hours; or about 36 hours.

In certain embodiments of the methods of the disclosure as disclosed herein, the obtained pure cannabinoid has the desired purity. In certain other embodiments, the methods of the disclosure comprise one or more additional purifications (e.g., the method comprises two or more, or at least two, or at least three, or no more than two, or no more than three successive purifications). For example, in certain embodiments, the methods of the disclosure as disclosed herein further include:

providing the pure cannabinoid and one or more second solvents selected from of N,N-dimethylacetamide, N,N-dimethylformamide, and tetrahydrofuran to obtain a second solution;

maintaining the second solution at a temperature between −40° C. to 0° C. for a time sufficient to obtain solid cannabinoid; and removing the one or more second solvents from the second solution to obtain cannabinoid having higher purity than the pure cannabinoid.

In certain embodiments of the methods of the disclosure as disclosed herein, the one or more second solvents are as described above with respect to the one or more solvents. For example, in some embodiments, the one or more second solvents is selected from of N,N-dimethylacetamide, N,N-dimethylformamide, and combination thereof. In some embodiment, the one or more second solvents is selected from of N,N-dimethylacetamide, tetrahydrofuran, and combination thereof. In some embodiments, the one or more second solvents is selected from of N,N-dimethylformamide, tetrahydrofuran, and combination thereof.

In certain embodiments of the methods of the disclosure as disclosed herein, the one or more second solvents is selected from of N,N-dimethylacetamide, N,N-dimethylformamide, tetrahydrofuran, and combination thereof, and further comprises water. For example, in certain embodiments, the one or more second solvents comprises N,N-dimethylacetamide and water.

Some embodiments of the methods of the disclosure as disclosed herein are those wherein the one or more second solvents is N,N-dimethylacetamide.

In some embodiments of the methods of the disclosure as disclosed herein, the one or more second solvents is N,N-dimethylformamide.

Some embodiments of the methods of the disclosure as disclosed herein are those wherein the one or more second solvents is tetrahydrofuran.

The pure cannabinoid (e.g., obtained after the first purification) and the one or more second solvents are provided in a weight ratio in a range of 5:1 and 1:5. In certain other embodiments, the pure cannabinoid and the one or more solvents are provided in a weight ratio in a range of 1:1 and 1:5; or in a range of 4:1 and 1:4; or in a range of 1:1 and 1:4; or in a range of 3:1 and 1:3; or in a range of 1:1 and 1:3; or in a range of 2:1 and 1:2; or in a range of 1:1 and 1:2; or in a range of 1.5:1 and 1:1.5; or in a range of 1:1 and 1:1.5; or in a range of 1.3:1 and 1:1.3; in a range of 1:1 and 1:1.3; or in a range of 1.1:1 and 1:1.1. In certain other embodiments, the pure cannabinoid and the one or more second solvents are provided in a weight ratio of about 1:1. In certain other embodiments, the pure cannabinoid and the one or more second solvents are provided in a weight ratio that is the same as the weight ratio of the plant material and the one or more solvents (e.g., ratio of the solute to the solvent is the same in the first purification and in the second purification; for example the weight ratio is about 1:1 for both purifications). In certain other embodiments, the pure cannabinoid and the one or more second solvents are provided in a weight ratio that is different than the weight ratio of the plant material and the one or more solvents (e.g., ratio of the solute to the solvent in the first purification is different from that in the second purification).

As with the first purification, the pure cannabinoid and the one or more second solvents, in certain embodiments, are provided under mixing at a temperature between 25° C. to 80° C., or between 30° C. to 50° C., for a time sufficient to prepare the solution (e.g., up to 1 minute, up to 5 minutes, up to 10 minutes, up to 1 hour, and even up to 2 hours), and/or under pressure of less than 1 atm, e.g., 0.75 atm, or 0.5 atm.

The second solution is maintained at temperature of up to 25° C. In certain embodiments of the methods of the disclosure as disclosed herein, the second solution is maintained at a temperature between −40° C. to −20° C.; or −40° C. to −25° C.; or −35° C. to −20° C.; or −35° C. to −25° C.; or −33° C. to −27° C.; or −32° C. to −28° C. Some embodiments of the methods of the disclosure as disclosed herein are those wherein the second solution is maintained at a temperature of about −30° C.

The second solution is maintained for a period of time sufficient to form solid cannabinoid. In certain embodiments, the second solution is maintained for a period of up to 6 hours, up to 8 hours, up to 12 hours, or 1 to 6 hours, or 1 to 8 hours, or 1 to 12 hours, 12 to 72 hours; or 24 to 48 hours; or 30 to 42 hours; or about 36 hours.

Another aspect of the disclosure provides a cannabinoid prepared according to method of the disclosure as described herein. In certain embodiments of this aspect, the cannabinoid is tetrahydrocannabinolic acid, cannabidiolic acid, cannabidiol, tetrahydrocannabivarin, or a combination thereof. In certain embodiments of this aspect, the cannabinoid is tetrahydrocannabinolic acid. In certain embodiments of this aspect, the cannabinoid prepared according to method of the disclosure as described herein has a purity of at least 95%.

Another aspect of the disclosure provides methods of preparing a pure cannabinol. Such methods include heating the pure cannabinoid prepared according to method of the disclosure as described herein to a temperature sufficient to decarboxylate the cannabinoid. In some specific embodiments, such methods include:

providing the *Cannabis* plant material and one or more solvents selected from of N,N-dimethylacetamide, N,N-dimethylformamide, tetrahydrofuran, and combination thereof to obtain a solution of the extract;

maintaining the solution at a temperature between −40° C. to 25° C. for a time sufficient to obtain solid cannabinoid;

removing the one or more solvents to obtain a pure cannabinoid; and heating the pure cannabinoid to a temperature sufficient to decarboxylate the cannabinoid to obtain the pure cannabinol.

In certain embodiments of this aspect, the cannabinol is tetrahydrocannabinol or cannabidiol. In certain other embodiments of this aspect, the cannabinol is tetrahydrocannabinol.

The temperature required to decarboxylate the cannabinoid will vary based on the cannabinoid. For example, decarboxylating tetrahydrocannabinolic acid to obtain is tetrahydrocannabinol requires heating to a temperature of about 150 degrees celcius under vacuum, and distillation of the cannabinoids happens at 198° C. to 200° C. under vacuum. Both decarboxylation and distillation of cannabinoids can be accomplished, for example, in a vacuum assisted 5 liter short-path distillation system.

Another aspect of the disclosure provides a cannabinol having a purity of at least 96%, wherein the cannabinol is prepared according to method of the disclosure as described herein.

In certain embodiments, the cannabinol of the disclosure has purity of at least 97%; or at least 98%; or at least 99%; or at least 99.5%; or at least 99.9%.

In certain embodiments, the cannabinol of the disclosure is tetrahydrocannabinol. In some embodiments, tetrahydrocannabinol obtained by the methods of the disclosure is clear in appearance upon visual inspection (e.g., has no residual color, such as residual yellow color).

Certain aspects of the disclosure are illustrated further by the following examples, which are not to be construed as limiting the disclosure in scope or spirit to the specific procedures and compounds described in them.

EXAMPLES

Example 1: Preparation of Crude Oil

Crude oil, having been extracted from raw *cannabis*, is first dewaxed through a multistep cooling and filtration process in solution with ethanol.

First, crude oil is dissolved in absolute (undenatured) ethanol at a dilution ratio of 1:24. Oil-ethanol solution is cooled to −60° C. and maintained at −60° C. for 72 hours. Oil-ethanol solution is then transferred to a −10° C. freezer and maintained at −10° C. for 12 hours. Oil-ethanol solution is then filtered using a vacuum assisted Buchner funnel and 2.5 micron glass fiber filter.

Filtrate solution is cooled −10° C. freezer and maintained at −10° C. for 12 hours. After 12 hours, the solution is then filtered using Buchner funnel as noted above.

Ethanol is removed from the filtrate at 30° C., high vacuum rotary evaporator. The residual ethanol is removed using high vacuum oven maintained at a temperature of about 32° C. to obtain dewaxed crude *cannabis* oil.

Example 2: General Crystallization Procedure

The dewaxed crude oil is dissolved in a solvent. If necessary, the solution is heated (at atmospheric pressure or under vacuum) to assist dissolution. The resulting solution is placed in a crystallization dish and cooled for 36 hours. The contents of the crystallization dish are transferred to a Buchner funnel and the residual solution is removed through vacuum filtration through a 20 μm qualitative filter.

The material from the Buchner funnel is collected and again dissolved in the same solvent. If necessary, the solution is heated (at atmospheric pressure or under vacuum) to assist dissolution. The resulting solution is placed in a crystallization dish and cooled for 36 hours. The contents of the crystallization dish are transferred to a Buchner funnel and the residual solution is removed through vacuum filtration through a 20 μm qualitative filter to obtain crystalline tetrahydrocannabinolic acid (THCA).

Example 3: Solvent Survey

Crystallization of THCA solvent survey study is carried out according the general procedure described above at 0° C. using crystalline THCA standard (rather than *cannabis* oil). Several solvents are evaluated and the crystallization results are provided in Tables 1 and 2. The solubility (g/mL) provided an indication of loading capacities: higher loading capacities are desirable to make the process more efficient. The theoretical yield of THCA is determined based on the purity of the standard, which was 97.4%.

Table 1 provides the yield for the crystalline THCA when the crystallization is performed at 0° C. These results indicate which solvents are viable at temperatures compatible with existing equipment. DMA, THF and DMF provided highest throughput and efficiency. In contrast, the current commercial and known purification methods utilizing single-solvent or multi-solvent evaporative crystallization with, e.g., hexane, pentane, isopropyl alcohol, ethanol and hydrocarbons, etc., achieve crystallization yields of 35-50%.

TABLE 1

Solvent Survey

| Solvent | Solubility (g/mL) 22.8° C. | 30° C. | 40° C. | Crystallization yield (%) |
|---|---|---|---|---|
| n-Propanol | 0.140 | 0.360 | 0.585 | 0 |
| DMA | 0.498 | 0.650 | 0.892 | 92.5 |
| THF | 0.743 | 1.057 | 1.324 | 84.2 |
| DMF | 0.612 | 0.929 | 1.171 | 81.5 |
| Heptane | 0.092 | 0.155 | 0.258 | 30.8 |
| 1-Butanol | 0.151 | 0.258 | 0.514 | 0 |
| Ethyl Acetate | 0.555 | 0.931 | 1.216 | 52.2 |
| Acetone | 0.818 | 1.063 | 1.440 | 0 |
| Acetonitrile | 0.562 | 0.953 | 1.230 | 0 |

Next, crystallization of dewaxed crude *cannabis* oil using DMA, THF, and acetonitrile is evaluated at several different temperatures. The results are provided in Table 2.

TABLE 2

Solvent Survey at different temperatures

| Solvent | Temperature (° C.) | Crystallization yield (%) |
|---|---|---|
| THF | 0 | 47.6 (n = 4)[1] |
| THF | −20 | 51.9 |
| THF[2] | −20 | 49.9 |
| Acetonitrile | −15 | 0 |
| DMA | 0 | 50.8 |
| DMA | −30 | 61.0 (n = 2)[3] |
| DMA | −20 | 92.5[4] |
| DMA | −30 | 94.3[4] |

[1] where n is provided, the percent yield represents average value.
[2] seeded with crystal of THCA
[3] lower quality source material (crude extract) containing a lower % of available THCA for crystallization
[4] higher quality source material (crude extract) having a higher % of available THCA for crystallization The results in Table 2 provide that THCA can be recovered from dewaxed crude *cannabis* oil material. The yields are even higher with using higher quality starting material, while seeding with THCA crystal did not improve yield.

Example 4: Purification Using DMA as Solvent

The dewaxed crude *cannabis* oil is added to N,N-dimethylacetamide at a 1:1 weight ratio, and the solution is heated to about 38° C. under vacuum to assist dissolution. The solution is mixed using high speed shearing mixer.

The resulting solution is then placed in a crystallization dish and cooled to −30° C. for 36 hours. The contents of the crystallization dish are then transferred to a Buchner funnel and the residual solution is removed through vacuum filtration through a 20 μm qualitative filter.

The material from the Buchner funnel is collected and again dissolved in N,N-dimethylacetamide at a 1:1 weight ratio based on weight of solid recovered from the first filtration. The solution is then heated to about 40° C. under vacuum to assist dissolution. The resulting solution is placed in a crystallization dish and cooled to −30° C. for 36 hours. The contents of the crystallization dish are transferred to a Buchner funnel and the residual solution is removed through vacuum filtration through a 20 μm qualitative filter.

The theoretical yield of THCA is based on 70.11% content of THCA in the dewaxed *cannabis* oil. After drying, crystalline THCA is obtained in 94% yield.

The crystalline THCA was subjected to single crystal X-Ray diffraction analysis. The single crystal X-Ray diffraction data was obtained by standard techniques using XtaLAB Synergy-S/Rigaku Oxford diffractometer operating with a Cu Kα radiation source at 50 kV, 1 mA. The scanning parameters ranged from 7.01 to 154.45° 2θ. The crystal was kept at 298.60(10) K during data collection.

Figure 1:
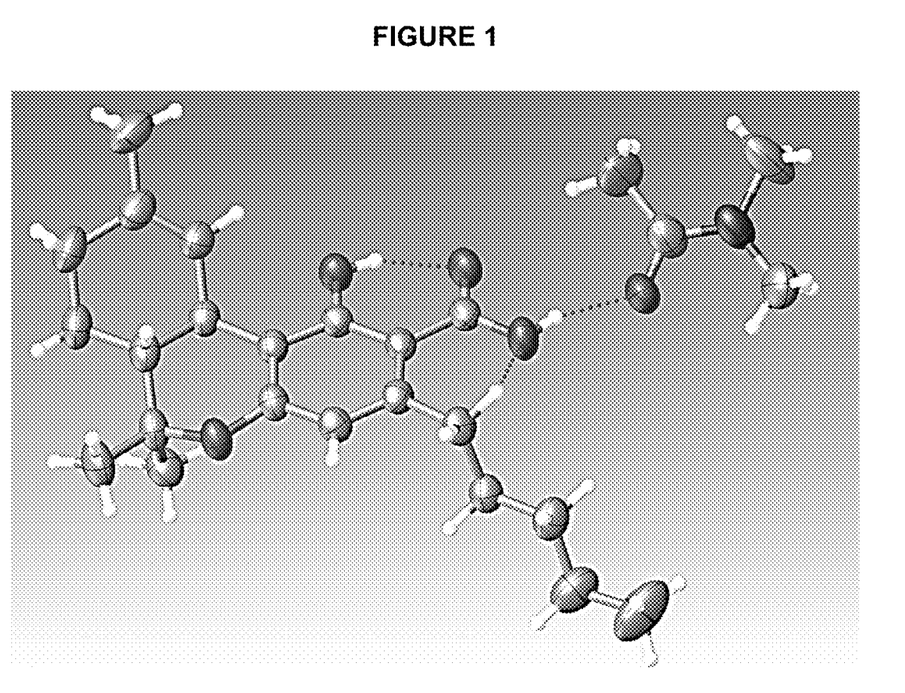
FIG. 1 shows single crystal X-ray structure of N,N-dimethylacetamide solvate of tetrahydrocannabinolic acid (Form A).

FIG. 1 shows single crystal X-ray structure of N,N-dimethylacetamide solvate of tetrahydrocannabinolic acid (Form A). The single crystal data for Form A is provided in Table 3, and the fractional atomic coordinates are listed in Table 4.

TABLE 3

Single Crystal Data for Form A

| | |
|---|---|
| Temperature/K | 298.60(10) |
| Crystal system | orthorhombic |
| Space group | P2$_1$2$_1$2$_1$ |
| a/Å | 9.4279(2) |
| b/Å | 10.8422(2) |
| c/Å | 25.2168(4) |
| α/° | 90 |
| β/° | 90 |
| γ/° | 90 |
| Volume/Å$^3$ | 2577.64(8) |
| Z | 4 |
| ρ$_{calc}$ g/cm$^3$ | 1.148 |
| μ/mm$^{-1}$ | 0.629 |
| F(000) | 968.0 |
| Crystal size/mm$^3$ | 40 × 200 × 100 |

TABLE 4

Fractional Atomic Coordinates (×10$^4$) and Equivalent Isotropic Displacement Parameters (Å$^2$ × 10$^3$).

| Atom | x | y | z | U$_{eq}$* |
|---|---|---|---|---|
| O1 | 5095(2) | 2840.6(16) | 5271.9(8) | 57.2(4) |
| O2 | 2197(2) | 4555.6(17) | 6621.6(7) | 58.0(5) |
| O3 | 1425(2) | 6753.2(19) | 6532.7(8) | 66.1(5) |
| O4 | 2079(3) | 7892.7(18) | 5851.7(8) | 70.3(6) |
| O5 | 588(3) | 9774.8(19) | 6148.9(9) | 76.3(7) |
| C13 | 3856(3) | 5961(2) | 5439.2(9) | 45.2(5) |
| C2 | 3004(3) | 4722(2) | 6179.9(9) | 45.0(5) |
| C1 | 3009(3) | 5865(2) | 5906.2(9) | 43.8(5) |
| C3 | 3779(2) | 3697(2) | 6012.3(9) | 44.1(5) |
| C11 | 4462(3) | 3802(2) | 5524.9(10) | 47.1(5) |
| C4 | 3856(3) | 2501(2) | 6323.0(10) | 49.6(5) |
| C12 | 4540(3) | 4928(2) | 5256.9(11) | 48.7(5) |
| C19 | 2127(3) | 6864(2) | 6121.9(10) | 50.1(5) |
| C15 | 3064(3) | 7165(2) | 4629.0(10) | 55.1(6) |
| N1 | −113(4) | 11436(3) | 6588.3(12) | 81.5(8) |
| C9 | 4938(3) | 1637(2) | 6062.3(12) | 55.5(6) |
| C22 | 3280(3) | 1255(2) | 5279.4(13) | 63.1(7) |
| C14 | 4050(3) | 7109(2) | 5105.7(11) | 53.1(6) |
| C5 | 4253(3) | 2649(3) | 6903.2(12) | 61.7(7) |
| C10 | 4772(3) | 1593(2) | 5464.6(12) | 56.3(6) |
| C16 | 3206(4) | 8371(3) | 4327.0(12) | 65.3(7) |
| C6 | 4970(4) | 1810(3) | 7169.3(14) | 73.3(8) |
| C21 | 5869(4) | 802(3) | 5193.5(15) | 74.5(9) |
| C23 | 431(5) | 10314(3) | 6569.6(15) | 78.6(9) |
| C8 | 4913(4) | 410(3) | 6355.3(15) | 73.9(9) |
| C26 | −444(5) | 12059(4) | 6095.2(16) | 88.3(11) |
| C17 | 2431(5) | 8419(4) | 3808.6(15) | 89.4(11) |
| C7 | 5435(5) | 604(3) | 6919.1(16) | 89.6(12) |
| C20 | 5419(6) | 1990(4) | 7736.8(15) | 101.6(14) |
| C25 | −233(8) | 12164(5) | 7073(2) | 131(2) |
| C24 | 868(11) | 9695(5) | 7082.3(18) | 162(4) |
| C18 | 2577(7) | 9677(6) | 3538(2) | 131(2) |

*U$_{eq}$ is defined as ⅓ of of the trace of the orthogonalised U$_{IJ}$ tensor.

X-Ray Powder Diffraction (XRPD) data was obtained by standard techniques using using Rigaku MiniFlex 600 diffractometer operating with a Cu Kα radiation source at 40 kV, 15 mA, step size 0.02° 2θ. The scanning parameters ranged from 3 to 60° 2θ. The XRPD data for Form A is provided in Table 5.

TABLE 5

| Peak No. | Wavenumber (cm$^{-1}$) | Absorbance intensity |
|---|---|---|
| 1 | 6.94 | 132557 |
| 2 | 11.64 | 68607 |
| 3 | 13.96 | 78720 |
| 4 | 14.2 | 24577 |
| 5 | 16.64 | 28130 |
| 6 | 18.74 | 29331 |
| 7 | 19.86 | 40961 |
| 8 | 20.76 | 70151 |
| 9 | 21.62 | 70375 |
| 10 | 23.48 | 22283 |
| 11 | 24.86 | 35775 |

Crystalline THCA is further subjected to distillation at 198-200° C. During the heating, decarboxylation of THCA occurs to give tetrahydrocannabinol (THC) in about 88% yield from THCA, and overall yield of 83% by weight from dewaxed *cannabis* oil (i.e., having 70.11% THC content). More importantly, the THC distillate is >98% pure and clear in appearance (i.e., has no residual color).

In contrast, common extraction methodologies, followed by distillation, result in THC having purity of less than 88% and overall yield from dewaxed *cannabis* oil of less than 55%. Notably, distilled THC always has a residual yellow appearance, which is undesirable, and all methods to mitigate the color (i.e., to remove the residual yellow appearance and arrive at clear product) further lower the overall yield of THC and/or increase contamination of in THC with various byproducts.

Example 5: Purification Using DMA in Various Amounts

The purification of the crude oil is performed according to Example 4 above, using various weight ratios of the crude oil and N,N-dimethylacetamide, and the results are provided in Table 3.

TABLE 3

| Run No. | Crude oil:DMA (weight:weight) | Crystallization yield (%) |
|---|---|---|
| 1 | 1:1 | 93.88 |
| 2 | 1:0.95 | 86.51 |
| 3 | 1:0.9 | 88.48 |
| 4 | 1:2 | 76.09 |
| 5[1] | 1:3 | 90.33 |
| 6[1] | 1:4 | 79.44 |

[1]seeded with crystal of THCA

Various aspects of the present disclosure are further exemplified by the non-limiting embodiments recited in the claims below. In each case, features of multiple claims can be combined in any fashion not inconsistent with the specification and not logically inconsistent.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A crystalline Form A of tetrahydrocannabinolic acid N,N-dimethylacetamide solvate.

2. The crystalline Form A of claim 1, characterized in that it provides the following cell unit parameters: space group is P2$_1$2$_1$2$_1$; cell dimensions are: a=9.4279(2) Å, b=10.8422(2) Å, c=25.2168(4) Å, α=β=γ=90°; and number of formula units are 4.

3. The crystalline Form A of claim 1, characterized in that it provides a XRPD pattern comprising peaks at about 6.9, about 11.6, about 14.0, about 20.8 and about 21.6 (2θ degrees).

Figure 2:
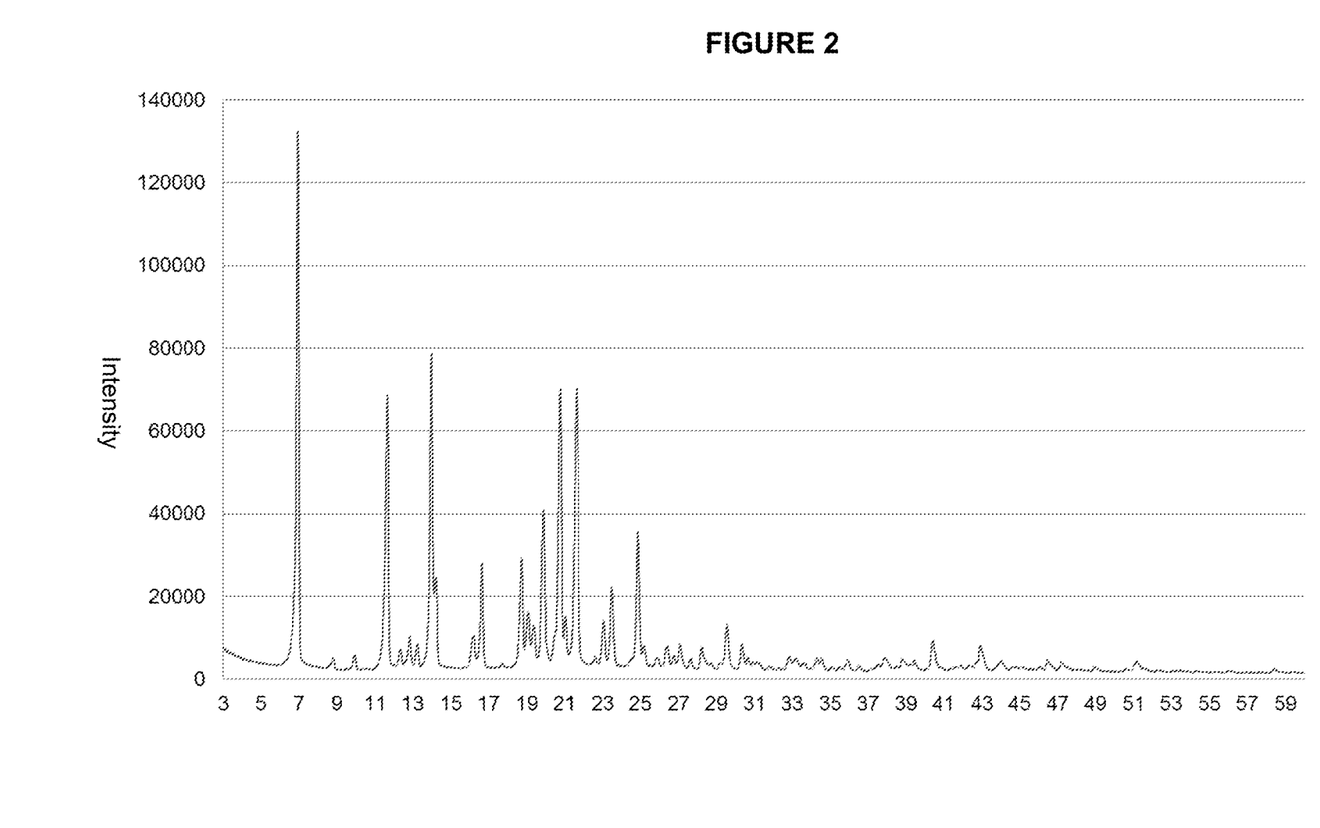
FIG. 2 shows a X-Ray Powder Diffraction (XRPD) pattern for the crystalline tetrahydrocannabinolic acid Form A as described herein.

4. The crystalline Form A of claim 1, characterized in that it provides a XRPD pattern in accordance with that shown in FIG. 2.

5. The crystalline Form A of claim 3, wherein the XRPD pattern further comprises peaks at about 14.2, about 16.6, about 18.7, about 19.9, about 23.5, and about 24.9 (2θ degrees).

* * * * *